United States Patent [19]

Huber

[11] Patent Number: 5,054,914
[45] Date of Patent: Oct. 8, 1991

[54] APPARATUS FOR ANALYSIS OF VOLATILE SAMPLES BY ATOMIC SPECTROSCOPY

[75] Inventor: Bernhard Huber, Uberlingen, Fed. Rep. of Germany

[73] Assignee: Bodenseewerk Perkin Elmer GmbH, Uberlingen, Fed. Rep. of Germany

[21] Appl. No.: 562,178

[22] Filed: Aug. 3, 1990

[51] Int. Cl.$^5$ ............................................. G01N 21/01
[52] U.S. Cl. ..................................... 356/36; 356/311
[58] Field of Search ................... 356/36, 311, 312, 315

[56] References Cited

FOREIGN PATENT DOCUMENTS 3226235 1/1984 Fed. Rep. of Germany .
3233130 3/1984 Fed. Rep. of Germany .
3830504 3/1990 Fed. Rep. of Germany .

OTHER PUBLICATIONS

Arenas et al., *Fresenius Zeitschrift fur Analytishe Chemie*, vol. 332, pp. 447–452.

Piwonka et al., *Fresenius Zeitschrift fur Analytishe Chemie*, vol. 321, 1985, pp. 225–234.

Alt et al., *Fresenius Zeitschrift fur Analytishe Chemie*, vol. 327, 1987, pp. 233–234.

*Primary Examiner*—F. L. Evans
*Attorney, Agent, or Firm*—Thomas P. Murphy; Edwin T. Grimes

[57] ABSTRACT

The volatile sample is entrained by a carrier gas flow leading to a measuring arrangement of an atomic spectrometer through a carrier gas conduit. A tube section containing a gas permeable, inert filling is placed in the carrier gas conduit. A cooling jacket is associated with this tube section. The volatile sample is frozen out and/or adsorbed at the filling. Subsequently, the filling is heated by at least one infrared radiator through the cooling jacket whereby the deposited volatile sample is vaporized and supplied to the measuring arrangement in concentrated manner.

5 Claims, 1 Drawing Sheet

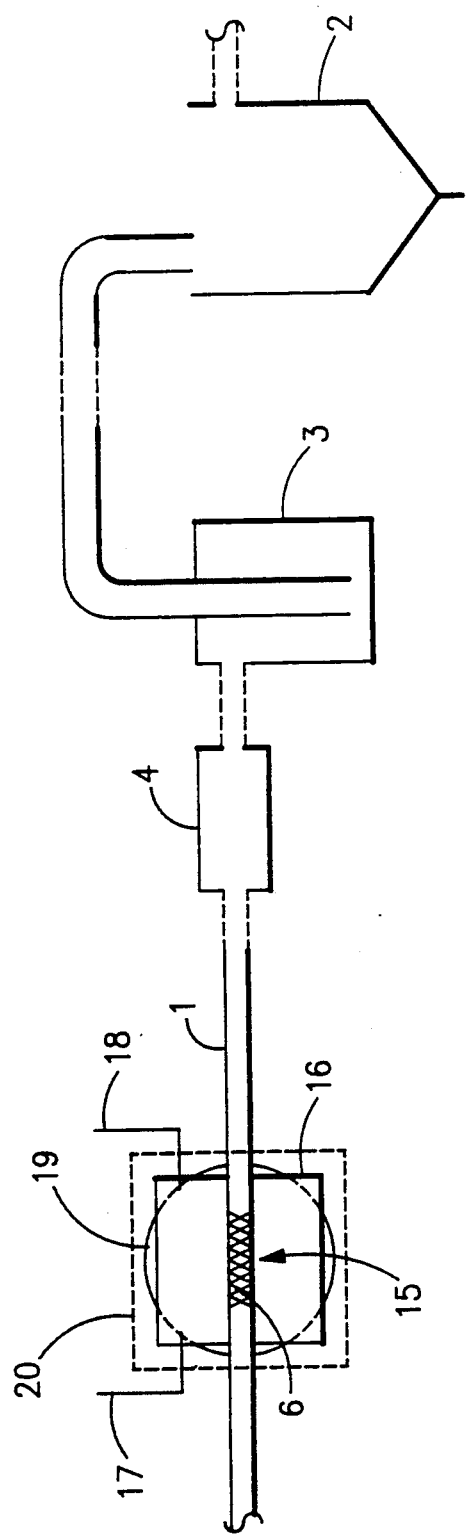

APPARATUS FOR ANALYSIS OF VOLATILE SAMPLES BY ATOMIC SPECTROSCOPY

FIELD OF THE INVENTION

The invention relates to atomic spectrometers and, more particularly to an apparatus for passing a volatile sample by means of a carrier gas into the measuring arrangement of an atomic spectrometer.

In its more particular aspects, the invention specifically relates to an apparatus for passing a volatile sample by means of a carrier gas into the measuring arrangement of an atomic spectrometer and which apparatus contains a carrier gas line or conduit for connection to a carrier gas source and for conducting a carrier gas flow containing the volatile sample through the carrier gas line or conduit towards the measuring arrangement. The carrier gas line or conduit comprises a tube section which is made of quartz and which is provided with a cooling jacket for throughpassing a coolant. In the region of the cooling jacket, the tube section contains a gas permeable filling for enriching the volatile sample. Heating means are associated with the tube section for heating the filling and vaporizing the volatile sample.

BACKGROUND OF THE INVENTION

From German Patent No. 3,226,235 it is known to produce a volatile sample by adding suitable reagents to a sample material, for example, one or more volatile hydrides of elements like arsenic and others by the addition of reducing agents. The volatile sample is entrained by a carrier gas flow, for instance, an inert gas flow and supplied to the measuring arrangement by means of a carrier gas line or conduit. In the measuring arrangement, the volatile sample contained in the carrier gas flow, is thermally decomposed and there is measured either the absorption or the emission of the atoms formed as the result of the thermal decomposition.

One problem of such known apparatus resides in the fact that the volatile sample is diluted by the carrier gas flow whereby the sensitivity of measurement is considerably impaired.

With regard to a similar apparatus for the analytical determination of volatile elements like mercury, it has been proposed, cf. German Published Patent Application No. 3,830,504.6, published Mar. 15, 1990, to bond the mercury vapor which is present in the carrier gas flow, to a gold wire net by amalgam formation. Subsequently, the amalgam is thermally decomposed by rapid heating by means of, for example, an infrared radiator and the mercury vapor is supplied to the measuring arrangement by the carrier gas flow. In addition to the heating device, there is provided cooling means for cooling down the carrier gas line or conduit as rapidly as possible after heating of the gold wire net in order to thereby render possible a high analysis frequency. The cooling means and the heating device may be series arranged with respect to the flow direction of the carrier gas and the carrier gas line or conduit, on the one hand, and the cooling means and the heating means, on the other hand, may be moveable relative to each other. However, there can also be provided a stationary arrangement in which the cooling means and the heating device are separated from each other during the cooling phase by means of a shield. When using the infrared radiator, the carrier gas line or conduit is made of a material such as fused silica which is transparent for infrared radiation, at least in the region of the gold wire net.

According to a publication by V. Arenas, M. Stoepler and G. Bergerhoff, entitled "Arsenic determination in the ultratrace range by atomic absorption spectrometry after preconcentration of the hydride", published in Fresenius Zeitschrift für Analytische Chemie, Vol. 332, pages 447 to 452, 1988, arsenic in the range of 0.05 to 6 ng is determined by atomic absorption spectroscopy using the hydride method. Therefore, the arsenic containing sample is reacted in a hydride reactor with sodium boron hydride and the addition of acid. The thus formed arsine is entrained in a helium current which is dried by freezing out water in a cold trap and which is passed, after the addition of hydrogen, through a further cold trap to the atomic absorption spectrometer. The further cold trap has the form of a U-shaped tube and is cooled to at least $-170°$ C.; it has contained therein a filling of silanized quartz wool at which the arsine is deposited. The cold trap is provided with a heater winding and can be heated from $-180°$ C. to $+200°$ C. in less than 10 seconds.

In accordance with a publication by J. Piwonka, G. Kaiser and G. Tölg, entitled "Determination of selenium at ng/g-and pg/g-levels by hydride generation-atomic absorption spectrometry in biotic materials", published in Fresenius Zeitschrift für Analytische Chemie, Vol. 321, pages 225 to 234, 1985, selenium in the range of 0.006 to 6 ng is determined by atomic absorption spectroscopy using the hydride method in a manner such that the selenium containing sample is reacted in a hydride reactor with sodium boron hydride and the addition of acid. The thus formed selenium hydride is entrained in an inert gas stream which is passed through an aerosol trap. Thereafter, the selenium hydride containing inert gas stream enters a straight quartz tube which is directly connected to the quartz cuvette of an atomic absorption spectrometer. A section of the straight quartz tube contains a filling of silanized Chromosorb W 30/60 (a diatomaceous earth-based adsorbent used in gas chromatography) or silanized quartz wool. This section is surrounded by an aluminum block cooled by liquid nitrogen. Upon termination of the reaction, the cooled aluminum block is removed and the adsorbed selenium hydride is desorbed by heating the tube section using a water bath or a furnace which is displaceable along the quartz tube. As a result of the abrupt release of the selenium hydride, there are obtained sharp peaks and correspondingly higher sensitivities.

A further publication by F. Alt, J. Messerschmidt and G. Tölg, entitled "A contribution towards the improvement of Se-determination in the pg-region by hydride AAS", published in Fresenius Zeitschrift für Analytische Chemie, Vol. 327, pages 233 to 234, 1987, relates to a similar system for determining selenium in the pg-region. In this system the adsorption section of the straight quartz tube is located within an electrically heatable steel tube which is present within a liquid nitrogen-filled quartz cooler during adsorption of the formed selenium hydride.

From German Published Patent Application No. 3,233,130, published Mar. 8, 1984, there is known a method of introducing a sample substance in fine distribution into a spectroscopic excitation source like, for example, a flame or plasma. The sample is subject to combustion or evaporation on a sample carrier within a chamber and the thus formed fine particles are drawn into the suction system of the excitation source through a nozzel. The chamber may be defined by a quartz tube in which the sample carrier is displaceably arranged and can be heated to the combustion or evaporation temperature of the sample by means of an infrared radiator.

SUMMARY OF THE INVENTION

It is one object of the invention to provide an apparatus of the initially mentioned type which permits freezing out and/or adsorbing and subsequently vaporizing the sample in a particularly compact arrangement immediately in the carrier gas line or conduit.

According to the invention, this and other objects are achieved by the provision of a new and improved construction of an apparatus for passing a volatile sample by means of a carrier gas into the measuring arrangement of an atomic absorption spectrometer and which new and improved construction is distinguished, among other things, by the features that the heating means constitute an infrared radiator arranged outside the cooling jacket and the tube section as well as the cooling jacket are made of fused silica transparent for infrared radiation.

It has been found that the inventive apparatus permits a virtually lossfree deposition of the volatile sample from the carrier gas flow and that infrared radiative heating, in turn, renders possible vaporizing the deposited volatile sample in a manner substantially free of losses and sufficiently rapidly for achieving a considerable enrichment of the volatile sample in the carrier gas flow although the infrared radiation must pass through the walls of the cooling jacket in addition to the wall of the carrier gas line or conduit.

BRIEF DESCRIPTION OF THE DRAWINGS

The single FIGURE of the drawing is a schematic illustration of an exemplary embodiment of the inventive apparatus.

DETAILED DESCRIPTION OF A PRESENTLY PREFERRED EMBODIMENT OF THE INVENTION

In the single FIGURE of the drawing, there is schematically illustrated an exemplary embodiment of the inventive apparatus and therein the means for producing the volatile samples as well as the measuring arrangement are not shown or not shown in any detail because they do not constitute part of the inventor. The means for producing the volatile sample may be, for instance, a reactor of the type as conventionally utilized for producing volatile hydrides. Various constructions of such reactors are described, for example, in the initially mentioned German Patent No. 3,226,235. Instead of the therein described reactors, there can also be employed correspondingly designed reactors in which volatile samples are produced from a sample material and the volatile sample can be separated and supplied to a measuring arrangement by means of a carrier gas flow. The measuring arrangement can be any measuring arrangement of the type permitting atomization of the volatile sample which is present in the carrier gas flow or stream and measurement of the absorption or emission of the atoms thus formed.

The embodiment which is schematically illustrated in the single figure of the drawing as a matter of example and not limitation, will be seen to comprise a carrier gas line or conduit 1 extending from a reactor 2 which is connected to a carrier gas source of, for example, an inert gas such as argon. The reactor 2 can be followed, as viewed in the flow direction of the carrier gas, by washing means 3 and drying means 4.

The carrier gas line or conduit 1 contains a tube section 15 which is made of fused silica or any other suitable material transparent for infrared radiation. This tube section 15 is surrounded by a cooling jacket 16 likewise made of a material such as, for example, fused silica which is transparent for infrared radiation. The cooling jacket 16 contains a discharge line or conduit 18 and can be connected through an infeed line or conduit 17 to a coolant source for passing a cooling fluid through the cooling jacket 16. The cooling fluid may be, for example, a circulating cooling fluid or a liquefied gas such as liquid nitrogen. The cooling fluid may also be produced by a cold source which operates according to the Joule-Thomson effect.

Heating means containing at least one infrared radiator 19 are associated with the tube section 15 of the carrier gas line or conduit 1. In order protect the heating means during the cooling period of the tube section 15, a protective shield 20 can be arranged between the cooling jacket 16 and the at least one infrared radiator 19.

Within the tube section 15 of the carrier gas line or conduit 1, there is disposed a filling 6. The filling 6 is structured, for example, in a net-like or otherwise gas permeable manner and made of a material which is inert relative to the volatile sample and preferably has good heat conductive or heat absorbing properties. The gas permeable filling 6 may be made, for instance, of metal but may also constitute an adsorbent, particularly activated carbon.

During operation of the inventive apparatus, the coolant is passed through the cooling jacket 16 after the tube section 15 has been flushed with the carrier gas. During this cooling phase of the operation, the sample material is reacted in the reactor 2 with formation of the volatile sample which is taken up or entrained by the carrier gas and, if desired, after passage through the washing means 3 and the drying means 4, frozen out and/or adsorbed at the cooled filling 6 in the tube section 15. After a predetermined reaction time, the coolant infeed is interrupted. During a subsequent heating phase of the operation, the tube section 15 containing the filling 6 which is charged with the volatile sample, is exposed to infrared radiation by the at least one infrared radiator 19 through the cooling jacket 16 and heated thereby. The good heat conductivity or heat absorption of the filling 6 ensures that the filling 6 is rapidly and substantially uniformly heated during this phase of the operation. Substantially the entire amount of the frozen out and/or adsorbed volatile sample is thereby vaporized or desorbed within a comparatively very short period of time. As a result, the volatile sample is passed by the carrier gas flow or current to the measuring arrangement substantially in the manner of a "plug" without being distributed through an excessive carrier gas volume prior to arriving at the measuring arrangement. There is thus obtained a high concentration of the volatile sample in the carrier gas and, consequently, a high measuring sensitivity.

The aforedescribed exemplary embodiment of the inventive apparatus ratus advantageously is constructed in a manner such that the apparatus can be readily combined with the initially mentioned apparatus operating according to the amalgam method for determining mercury.

Although a certain particular embodiment of the invention is herein disclosed for purposes of explanation, further modification thereof, after study of this specification, will be apparent to those skilled in the art to which the invention pertains. Reference should accordingly be had to the appended claims in determining the scope of the invention:

What is claimed is:

1. An apparatus for passing a volatile sample into the measuring arrangement of an atomic spectrometer by means of a carrier gas, comprising:

a carrier gas conduit for connection to a carrier gas source;

said carrier gas conduit serving for connection to the measuring arrangement and for conducting therethrough to said measuring arrangement, a carrier gas flow containing the volatile sample;

a tube section made of fused silica which is transparent for infrared radiation;

said tube section constituting part of said carrier gas conduit;

a cooling jacket associated with said tube section;

said cooling jacket being adapted for connection to a cold source and for passing therethrough a coolant for cooling said tube section;

said cooling jacket being made of fused silica which is transparent for infrared radiation;

a gas permeable filling present in said tube section for depositing the volatile sample at said gas permeable filling during a cooling phase of the operation of the apparatus;

heating means associated with said tube section for vaporizing the volatile sample from said gas permeable filling during a heating phase of the operation of the apparatus; and said heating means containing at least one infrared radiator disposed outside said cooling jacket.

2. The apparatus as defined in claim 1, wherein:

said filling is made of a material which is inert relative to said volatile sample and has good heat conductivity.

3. The apparatus as defined in claim 2, wherein:

said filling is made of a metal which is inert relative to said volatile sample.

4. The apparatus as defined in claim 1, wherein:

said filling constitutes an adsorbent which is inert relative to the volatile sample; and said adsorbent is activated carbon.

5. The apparatus as defined in claim 1, further including:

a protective shield placed between said least one infrared radiator and said cooling jacket; and said protective shield being present between said at least one infrared radiator and said cooling jacket during said cooling phase of the operation of the apparatus.

* * * * *